(12) United States Patent
Chen et al.

(10) Patent No.: US 8,317,733 B2
(45) Date of Patent: Nov. 27, 2012

(54) ELECTROMAGNETIC MASSAGE HEAD AND HUMAN-LIKE MASSAGER COMPOSED BY ELECTROMAGNETIC MASSAGE HEADS

(75) Inventors: Shu-Mu Chen, Sanchong (CN); Khositmamit Vasu, Sanchong (CN)

(73) Assignees: Shu-Mu Chen (TW); Qiang Zhang (CN)

( * ) Notice: Subject to any disclaimer, the term of this patent is extended or adjusted under 35 U.S.C. 154(b) by 872 days.

(21) Appl. No.: 12/427,044

(22) Filed: Apr. 21, 2009

(65) Prior Publication Data

US 2010/0179456 A1 Jul. 15, 2010

(30) Foreign Application Priority Data

Jan. 13, 2009 (CN) ................. 2009 2 0000867 U

(51) Int. Cl.
*A61H 1/00* (2006.01)
*A61H 5/00* (2006.01)
*A61H 7/00* (2006.01)
*A61H 15/00* (2006.01)

(52) U.S. Cl. ............... 601/19; 601/15; 601/93; 601/113
(58) Field of Classification Search .................. 601/46, 601/112, 113, 115, 116, 122, 126, 127–131, 601/15, 78, DIG. 4, 53, 80, 84, 89, 93, 94–95, 601/134; 607/80, 88, 96; 401/6, 7, 8
See application file for complete search history.

(56) References Cited

U.S. PATENT DOCUMENTS

| | | | |
|---|---|---|---|
| 8,128,583 B2* | 3/2012 | Ghatge | 601/134 |
| 2004/0193077 A1* | 9/2004 | Hsu et al. | 601/49 |
| 2005/0015030 A1* | 1/2005 | Bousfield et al. | 601/113 |

* cited by examiner

*Primary Examiner* — Patricia Bianco
*Assistant Examiner* — Ophelia Hawthorne
(74) *Attorney, Agent, or Firm* — Garcia-Zamor IP Law; Ruy M. Garcia-Zamor

(57) ABSTRACT

An electromagnetic massage head which may be used as part of a human massager preferably includes a strong electromagnetic rotating head fixed together with an electromagnetic screw. The electromagnetic screw is configured to rotate in an axial direction. The operation of the strong electromagnetic head can achieve the effect of knead, massage, knock and shake etc. when used to provide massage treatment.

10 Claims, 5 Drawing Sheets

ELECTROMAGNETIC MASSAGE HEAD AND HUMAN-LIKE MASSAGER COMPOSED BY ELECTROMAGNETIC MASSAGE HEADS

TECHNICAL FIELD

This utility model relates to a massage head, especially, an electromagnetic massage head and a human-like massager composed by electromagnetic massage head.

BACKGROUND ART

Currently, familiar massagers are all through vibrating caused by the running of off-center motor. This kind of massager can lead the movements of skin and subcutaneous fat through vibrating to achieve the effect of losing weight and generating heat. However, because nerves and points of human-body are protected by muscular tissue, this kind of massage mentioned above can only bring the vibration of skin but not nerves and points. On the contrary, high speed rotating of motor will quickly scrubbing the skin, which will cause rashes and itching.

Certainly, we saw some magnetic massagers on the market. It can realize a certain magnetotherapy effect by acting on nerves of human body through the magnetic force of magnets installed on the massage head. However, it cannot really meet people's daily requirement because of its singular function and great difference to real person knead, nip, massage, knock and shake.

CONTENTS OF THE INVENTION

Aiming at the shortcomings above in existing technology, this utility model is to provide a human-like magnetic massage heads and a human-like massager composed by massage heads which can realize the function of magnetotherapy, knead, nip, massage, knock and shake For achieving the objective above, this utility model adopts the following technical solution:

An electromagnetic massage head, comprising a strong electromagnetic rotating head and an electromagnetic screw which is equipped with a rotating axial driving part and a fixing part. The strong electromagnetic rotating head is fixed together with the electromagnetic screw rotating driving part and driven by electromagnetic screw rotating in an axial direction.

The mentioned strong magnetic rotating head comprising shell and several strong magnetic beads. The surface of the shell upper cover was equipped with some spherical holes whose quantity is the same as and radius is less than that of the strong magnetic beads. The strong magnetic bead is popped out on the surface of shell upper cover through holes.

The strong magnetic beads mentioned are equipped with elastic supporting equipment with magnetic beads' salver, spring and cavity for orientating spring included. The spring orientation cavity was fixed on the under cover of shell. The spring is installed in the cavity and its upper end is hold under the magnetic beads' salver.

The mentioned electromagnetic screw comprises upper cover, rotating iron core and loop. The external surface of the rotating iron core is equipped with helix groove while the inner of upper cover is equipped with a salient assorted with the helix groove. The upper end of the rotating iron core is fixed with the strong electromagnetic rotating head.

There are two helical grooves for the rotating iron core external surface mentioned. They separately start from the two ends of the diameter of iron core upper surface and spreading to the below end by a circulation of 180. The interior of the upper cover has two salient assorted with the helical groove.

The electromagnetic screw mentioned also includes rotating iron core restoring spring whose upper end supports upper cover while under end is hold under the circle salient of rotating iron core end.

The loop mentioned includes loop itself and spool.

The middle cavity end of the loop spool mentioned is equipped with cushion rubber mat.

A human like massage machine massage machine itself and several electromagnetic massage head and central control equipment. The electromagnetic massage head staggered on the surface of massage machine horizontally and vertically. Every electromagnetic massage head is controlled by the central control equipment independently and comprises of strong electromagnetic rotating head and electromagnetic screw. The electromagnetic screw is equipped with a rotating axial driving part and a fixing part. The strong electromagnetic rotating head is fixed together with the electromagnetic screw rotating driving part and drived by electromagnetic screw rotating in an axial direction.

The strong magnetic rotating heads mentioned include shell and several strong magnetic beads. On the surface of the shell, there is a spherical through hole equipped whose radius are less than the corresponding strong magnetic beads. The strong magnetic beads is popped out to the up cover surface of the shell by spherical through hole. All the strong magnetic beads corresponded are equipped with elastic supporting equipment which comprises magnetic beads salver, spring and cavity for orientating spring included. The spring orientation cavity was fixed on the under cover of shell. The spring is installed in the cavity and its upper end is hold under the magnetic beads salver. The electromagnetic screw stated comprises upper cover, rotating iron core, rotating iron core restoring spring, amortizing rubber mat, loop and loop spool. There are two helical groove equipped on the rotating iron core external surface. They separately start from the two ends of the diameter of iron core upper surface and spreading to the below end in parallel. The interior of the upper cover has two salient assorted with the helical groove while the rubber mat is equipped in the bottom of loop spool midplane.

By adopting the structure stated above, the electromagnetic massage head and the human-like massager composed by electromagnetic massage heads of this utility model, after being electrified, will rotate under the action of central control equipment's control and loop magnetic force while its iron core is pulled out in an axial direction and via screw groove and the upper cover of electromagnetic screw's salient, can achieve the effect of knead, nip, massage, knock and shake the massage place and verily realize the human-like deep massage. In addition, the magnetic force of strong magnetic bead has a certain force for releasing the pain of joint and fatigue by acting on physical points and nerve.

MODE OF CARRYING OUT THE INVENTION

Figure 1:
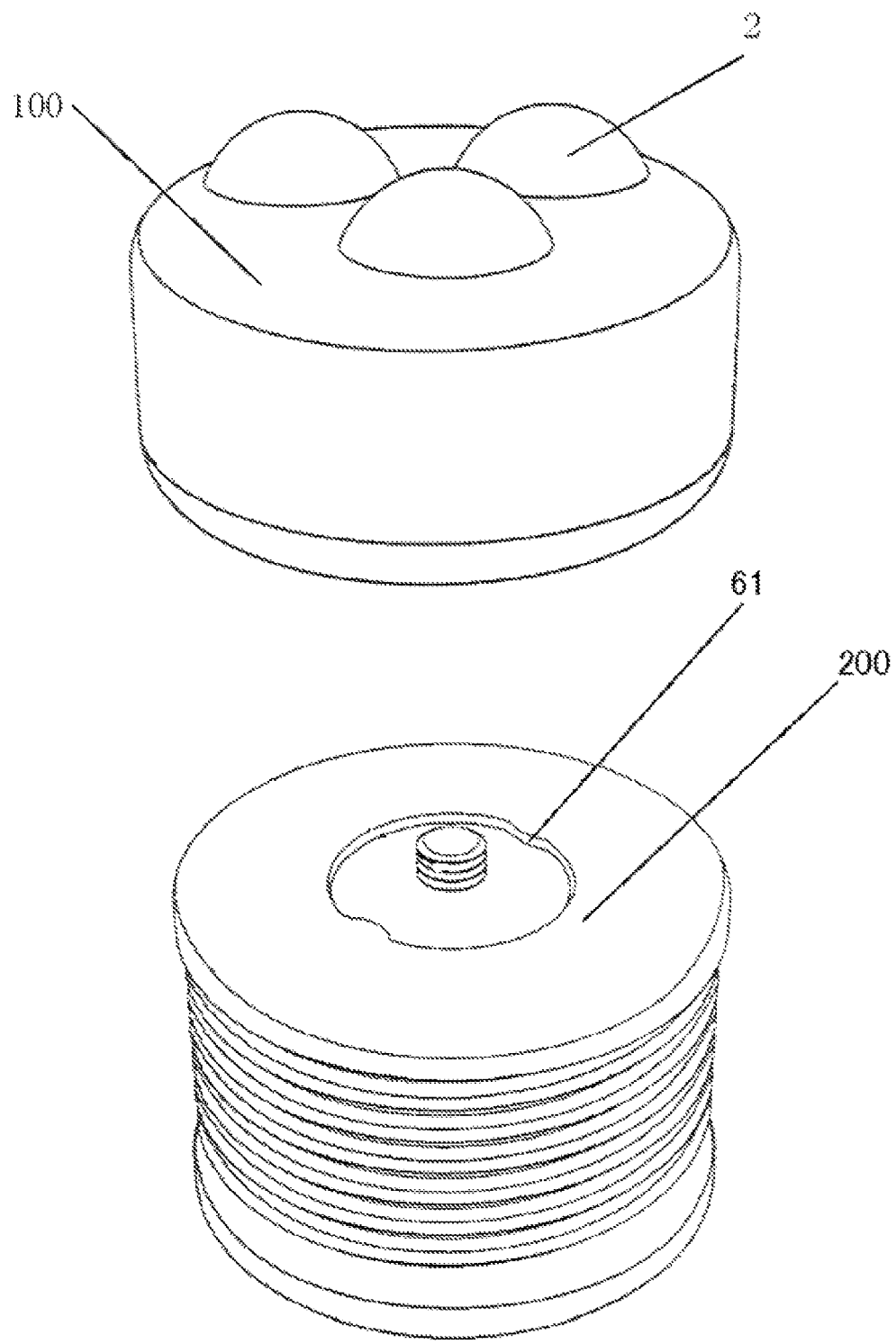
FIG. 1 is a breakdown drawing of magnetic massage heads, in accordance with the utility model.
Figure 2:
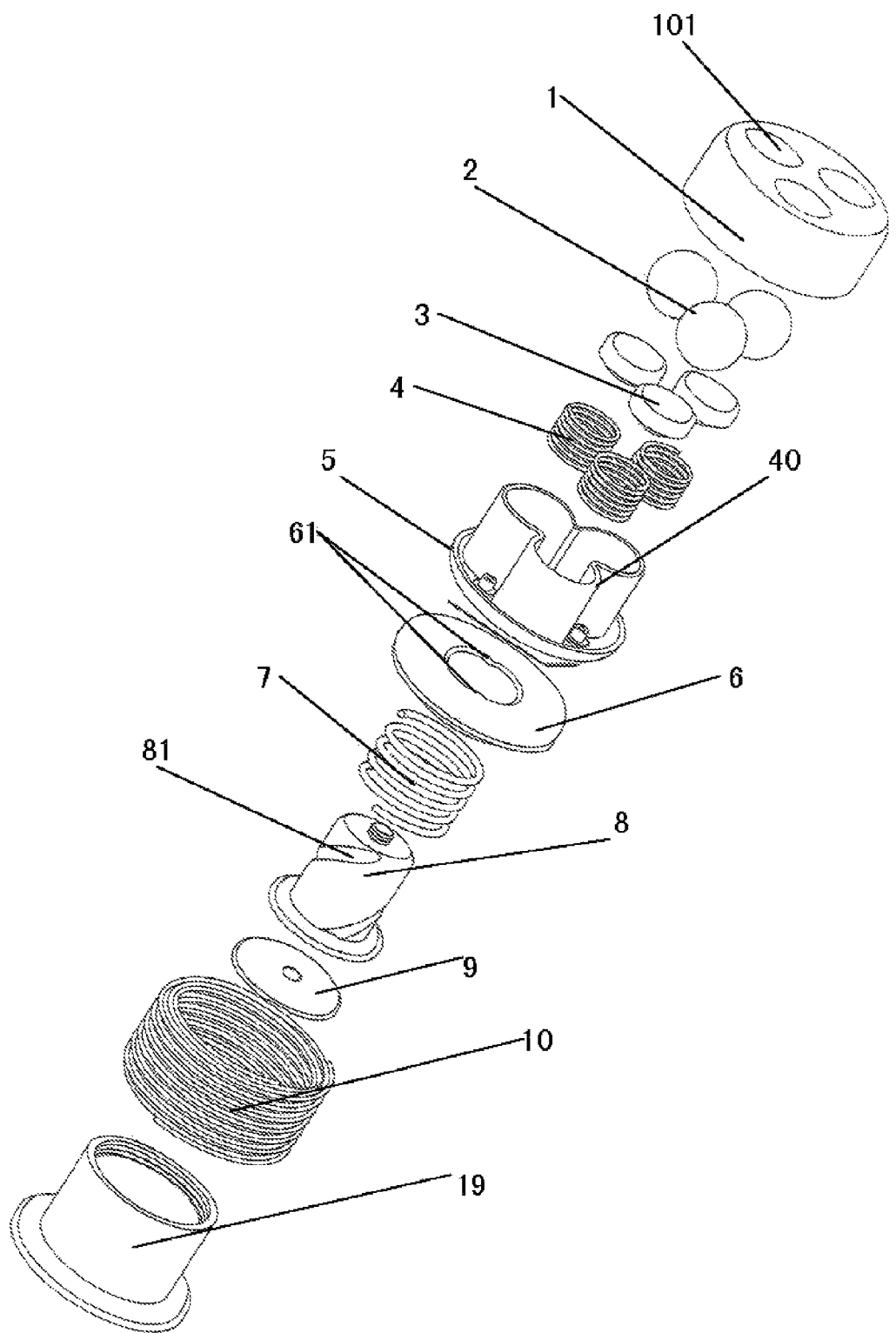
FIG. 2 is an exploded view of the magnetic massage heads of the utility model.

Further explanation to the invention will be stated below combining with the attached figures and the mode of carrying out the invention As shown in FIG. 1 and FIG. 2, the magnetic massage head comprises strong magnetic rotating head 100 and magnetic screw 200, hereinto strong magnetic rotating head includes shell 1 and strong magnetic bead 2. The upper cover surface of the shell 1 was equipped with some through holes 101 whose quantity is the same as and radius is less than that of the strong magnetic beads. Inside of the shell 1, there is an elastic supporting equipment equipped which comprises magnetic beads salver 3, spring 4 and cavity 40 for orientating spring included. The spring orientation cavity 40 was fixed on the under cover 5 of the shell. The spring 4 is installed in the cavity 40 and its upper end is hold under the magnetic beads salver 3. The strong magnetic bead 2 is popped out on the surface of shell 1 upper cover through holes 101.

The magnetic screw 200 mainly includes rotating iron core 8, loop, upper cover 6, hereinto loop is comprised by loop itself 10 and loop spool 19. The external surface of the rotating iron core 8 is equipped with two helical groove 81 which separately start from the upper end surface diameter of iron core 8 and spreads to the below end by a circulation of 180. The interior of the upper cover 6 has two salient 61 assorted with the helical groove 61. The loop itself 10 is equipped on the loop spool 19 which is equipped with a rubber mat 9 on the bottom of midplane. Rotating iron core 8 is equipped in the cavity of loop spool 19. The restoring spring 7 is equipped in the cavity of loop spool 19. Its upper end supports upper cover 6 while below end supports circle salient of rotating iron core 8 end.

After the fixation of strong magnetic rotating head 100 and magnetic screw 200, when the central control system gives a pulse signal to the magnetic massage head, the iron core 8 will drive the strong magnetic rotating head 100 to do 180 movement in axial direction by electrifying the loop. After the vanishing of signal, the iron core 8 will be re-located in the loop by the restoring spring 7. Continuous sorts of pulse can control iron core 8 to do kinds of speed movement, thus the strong magnetic rotating head 100 can realize kinds of massage movement.

Along with the rotation of strong magnetic rotating head 100, the spherical strong magnetic bead 2 can offset the interface friction by self rotation When the interface of strong magnetic rotating head 100 is non-flat, the lengthen and shorten of spring 4 can adjust the height of spherical strong magnets 2 to the best exposure effect with human body. The spheric magnets will make full use of magnets physical property and act on body meridian, point or parts in order to achieve the treatment effect of magnetic field physiatrics.

Magnetic massage head mentioned in this unity model are staggered horizontally and vertically on the massager itself. The central control system is connected separately by electricity with every magnetic massage head to control every magnetic massage head independently.

When the human-like massager is working, magnetic field will be generated by electrifying the loop and then iron core 8 will be pushed out because of magnetic effect. Two screw salients 81 on the iron core itself will be cooperated with upper cover 6, which makes iron core 8 running outside and at the same time drive iron core 8 to make a 180 rotation. Because magnetic rotating head is locked tightly with iron core 8, the strong magnetic rotating head 100 will also keep rotating 180.

When the power of loop is cut, the elasticity of restoring spring 7 will press iron core 8 to its original location. Samely because of the operation of screw salient and upper cover 6, iron core 8 itself will a reversal 180 rotation.

Figure 3:
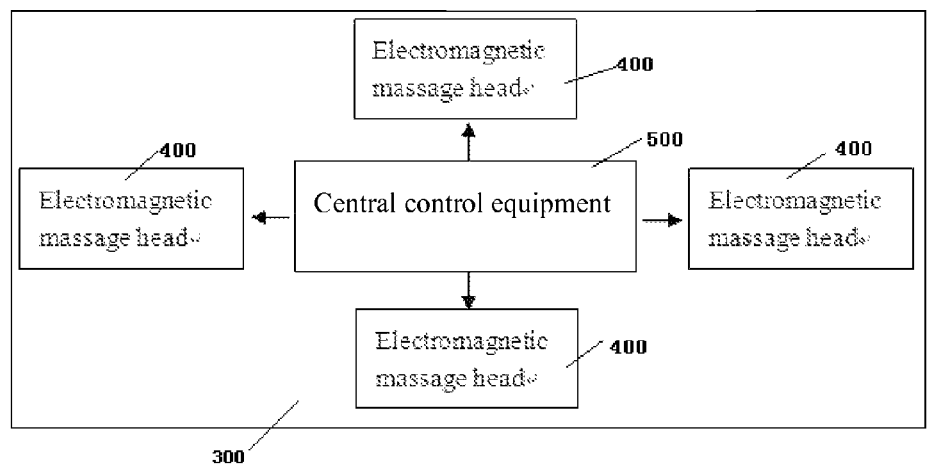
FIG. 3 is an illustrative diagram of the magnetic massage heads of the utility model.

As shown in FIG. 3, the massage effect mentioned in this implementation example can control its massage function through the pulse signal sent out by central control system When the central control system sends out a long square wave to any magnetic massage head, iron core 8 will be popped out because of magnetic field effect to realize the shiatsu effect while its time is upto the length of square wave.

When the central control system sends out a short square wave to any magnetic massage head, iron core 8 will be drawn back because of magnetic field effect to realize the beating effect while its speed is upto the frequency of square wave.

When the central control system sends out a short sawtooth wave to any magnetic massage head, iron core 8 will be drawn back and popped out quickly because of magnetic field effect to realize the vibrating effect while its speed is upto the frequency of sawtooth wave.

When the central control system sends out a sine wave to any magnetic massage head, the pop-up strength of iron core 8 will be gradually increased and decreased to realize the gentle touch effect while its speed is up to the frequency of sawtooth wave. The strong magnetic rotating head will be rotated 180 positively and negatively to realize massage effect. The central control system can imitate all the human-like massage effect through control one or many magnetic massage head by sending out different waves.

"In FIG. 4 individual massage heads are identified with numerals 11, 12, 13, 14, 21, 22, 23 , 24, 25, 31, 32, 33, 34, 41, 42, 43, 44, 45, 51, 52, 53, and 54 so that the below outlined sequences can be understood in conjunction with the drawing. For example, in the below sequence of 11 →22 →21 indicates that one possible pattern of motion of the massage heads is for head 11 to move first, then head 22, and then head 21."

Figure 4:
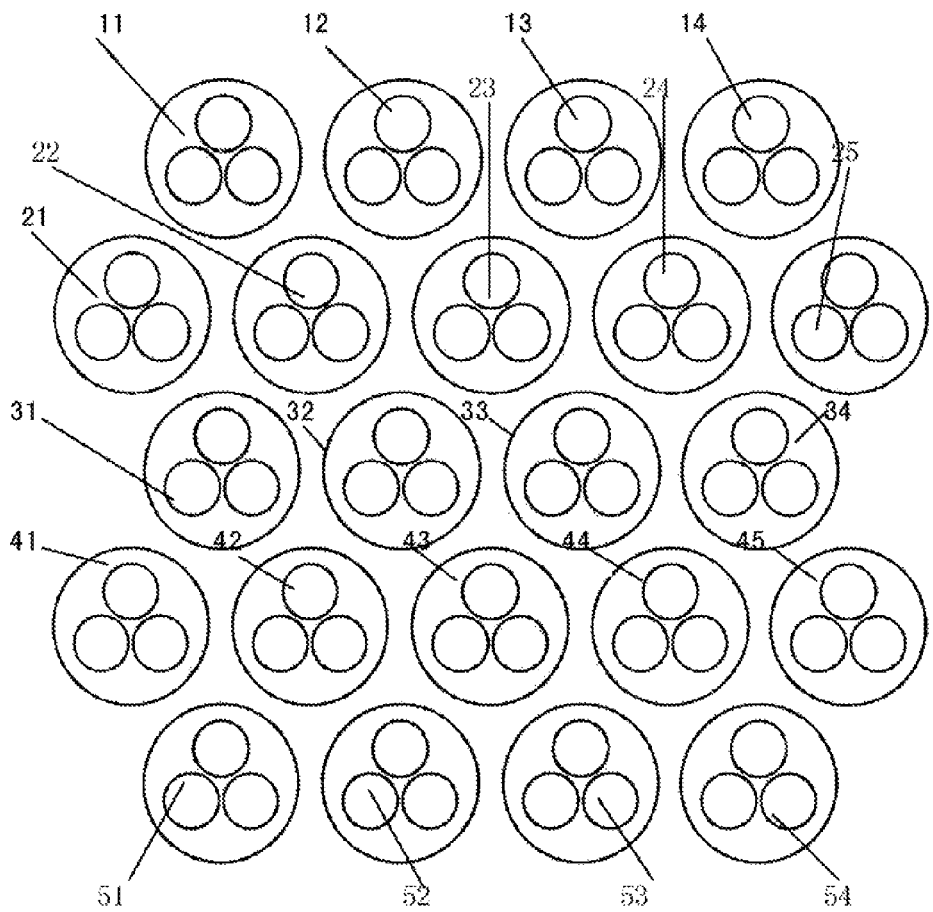
FIG. 4 is a sketch map of the magnetic massage heads of the utility model.
Figure 5:
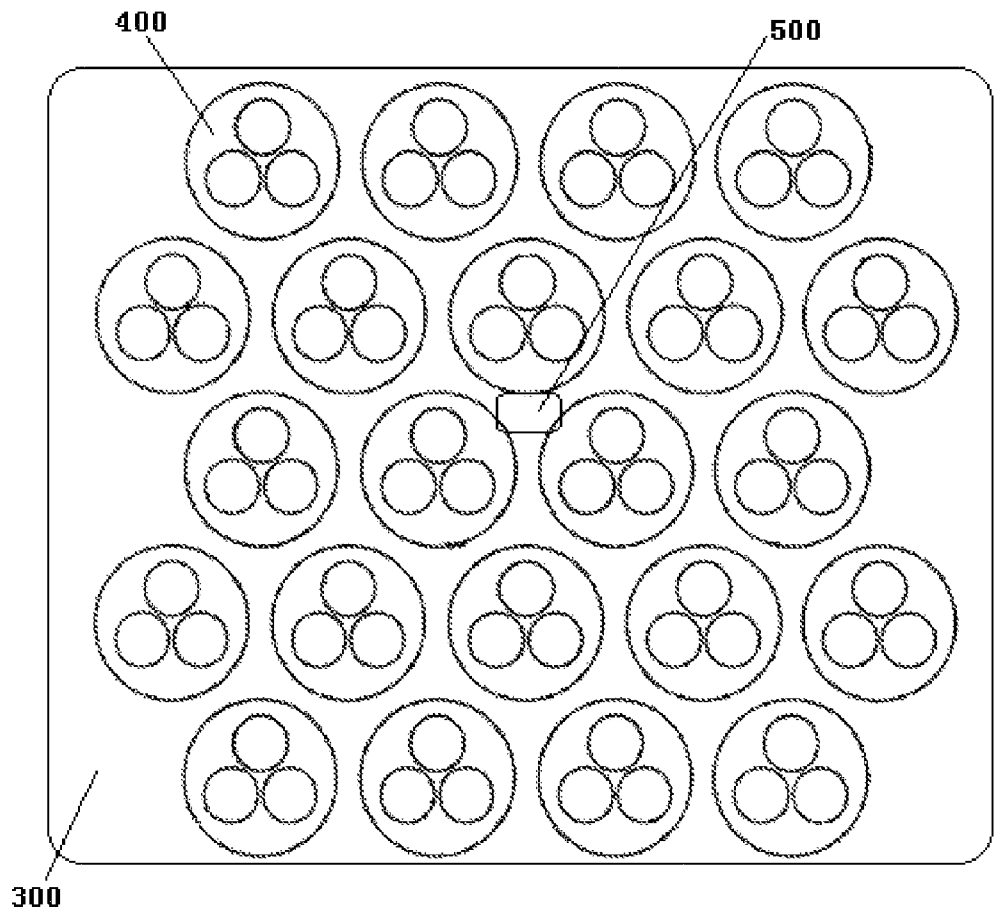
FIG. 5 is a schematic diagram of a human massager 300 illustrating central control equipment (also referred to in the specification as "central control system") 500 and electromagnetic massage head 400.
Figure 6:
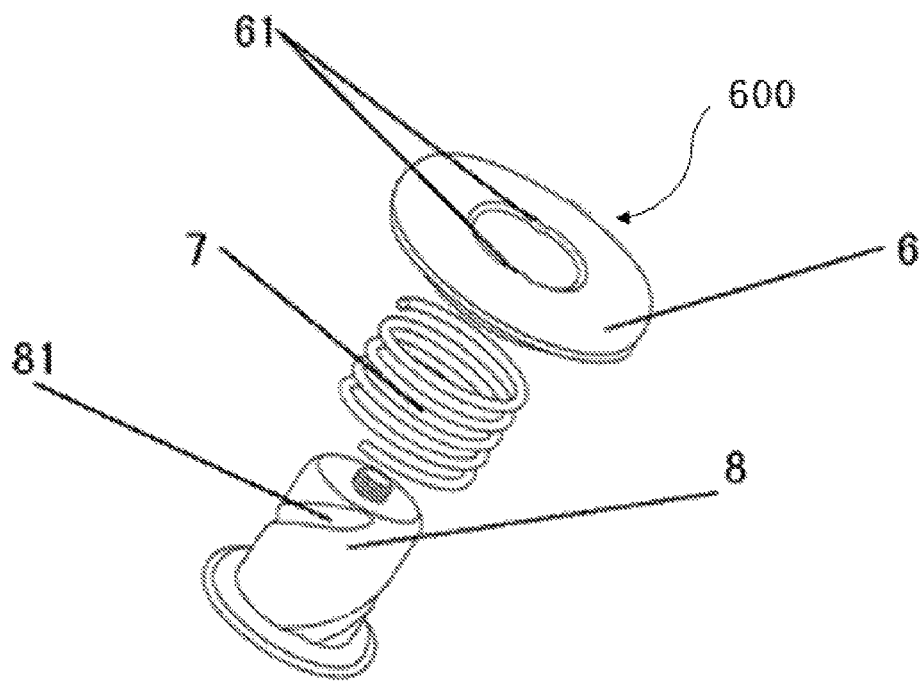
FIG. 6 illustrates a rotating axial drive part 600.
Figure 7:
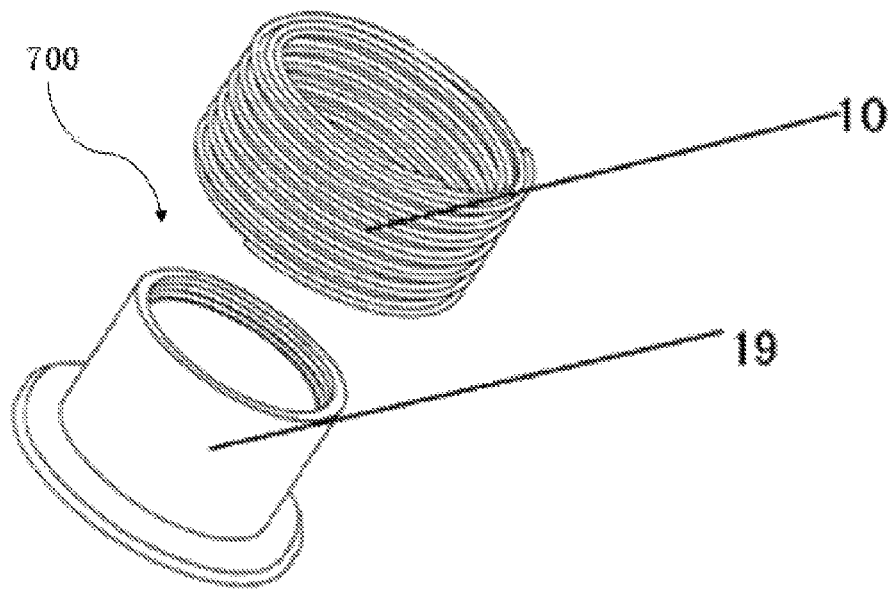
FIG. 7 illustrates a fixing part 700.

This implementation example realizes the following stated massage types according to the collocation of kinds of pulse signal as what is shown in FIG. 4:

11→22→21 positive revolving massage

11→21=>22 negative revolving massage (21+25)→(22+24)→23 from outside jostling

23→(22+24)→(21+25) from inside widening (11+12+13+14)→(21+22+23+24+25)→(31+32+33+ 34)→(41+42+43+44+45)→(51+52+53+54) or (51+52+53+54)→(41+42+43+44+45)→(31+32+ 33+34)→(21+22+23+24+25)→(11+12+13+14) to carry out to-and-fro massage Except the massage type stated above, kinds of other massage types can be realized by controlling pulse signal which brings the users higher quality of massage enjoyment.

The invention claimed is:

1. An electromagnetic massage head, comprising a strong electromagnetic rotating head and an electromagnetic screw which is equipped with a rotating axial driving part and a fixing part, the strong electromagnetic rotating head being fixed together with the electromagnetic screw rotating driving part and drivable by the electromagnetic screw rotating in an axial direction, wherein the strong magnetic rotating head comprises a shell and several strong magnetic beads, the surface of the shell upper cover being equipped with a plurality of spherical holes corresponding in number but having a radius which is less than that of the strong magnetic beads, the strong magnetic bead projecting through holes in a surface of the shell upper cover, the strong magnetic beads are equipped with elastic supporting equipment with magnetic beads' salver, and including a spring and a cavity for orientating the spring, the spring orientation cavity being fixed on the under cover of the shell, the spring being installed in the cavity and its upper end being held under the magnetic beads' salver, the electromagnetic screw includes an upper cover, rotating iron core and loop, the external surface of the rotating iron core being equipped with a helical groove and the inner surface of the upper cover being equipped with a salient assorted with the helical groove, the upper end of the rotating iron core being fixed with the strong electromagnetic rotating head.

2. The electromagnetic massage head as set forth in claim 1 wherein there are two helical grooves for the external surface of the rotating iron core, each helical groove being starting separately from the two ends of the diameter of an iron core upper surface and spreading to the lower end with a rotation of at least 180 degrees, an interior of the upper cover having two salient assorted with the helical groove.

3. The electromagnetic massage head as set forth in claim 2 wherein the loop includes a loop element and a loop spool.

4. The electromagnetic massage head as set forth in claim 3 wherein a middle cavity end of the loop spool is equipped with a cushion rubber mat.

5. The electromagnetic massage head as set forth in claim 1 wherein the electromagnetic screw also includes a rotating iron core restoring spring whose upper end supports the upper cover whilst its under end is held under the circle salient of rotating iron core end.

6. The electromagnetic massage head as set forth in claim 1 wherein the loop includes a loop element and a loop spool.

7. A human massager, comprising,
a plurality of electromagnetic massage heads comprising at least one strong electromagnetic rotating head and an electromagnetic screw which is equipped with a rotating axial driving part and a fixing part, the strong electromagnetic rotating head being fixed together with the electromagnetic screw rotating driving part and drivable by the electromagnetic screw rotating in an axial direction, wherein the strong magnetic rotating head comprises a shell and several strong magnetic beads, the surface of the shell upper cover being equipped with a plurality of spherical holes corresponding in number but having a radius which is less than that of the strong magnetic beads, the strong magnetic bead projecting through holes in a surface of the shell upper cover, the strong magnetic beads are equipped with elastic supporting equipment with magnetic beads' salver, and including a spring and a cavity for orientating the spring, the spring orientation cavity being fixed on the under cover of the shell, the spring being installed in the cavity and its upper end being held under the magnetic beads' salver, the electromagnetic screw includes an upper cover, rotating iron core and loop, the external surface of the rotating iron core being equipped with a helical groove and the inner surface of the upper cover being equipped with a salient assorted with the helical groove, the upper end of the rotating iron core being fixed with the strong electromagnetic rotating head, and central control equipment, the electromagnetic massage heads being staggered on the surface of massage machine horizontally and vertically, every electromagnetic massage head being controlled by the central control equipment independently.

8. A human massager as set forth in claim 7 wherein the electromagnetic screw further comprises an upper cover, rotating iron core, further comprises a rotating iron core restoring spring, amortizing rubber mat, loop and loop spool, two helical grooves being provided on the external surface of the rotating iron core, each groove separately starting from two ends of the diameter of iron core upper surface and extending to the lower end in parallel, an interior of the upper cover having two salient assorted with the helical grooves, and the rubber mat being provided at the bottom of loop spool on the midplane.

9. A human massager, comprising: an electromagnetic massage head, having a strong electromagnetic rotating head and an electromagnetic screw which is equipped with a rotating axial driving part and a fixing part, the strong electromagnetic rotating head being fixed together with the electromagnetic screw rotating driving part and drivable by the electromagnetic screw rotating in an axial direction, and central control equipment, the electromagnetic massage heads being staggered on the surface of massage machine horizontally and vertically, every electromagnetic massage head being controlled by the central control equipment independently and comprising a strong electromagnetic rotating head and electromagnetic screw, the electromagnetic screw being equipped with a rotating axial driving part and a fixing part, the strong electromagnetic rotating head being fixed together with the electromagnetic screw rotating driving part and driven by the electromagnetic screw rotating in an axial direction, wherein the strong magnetic revolving head includes a shell and several strong magnetic beads, a surface of the shell having a spherical through hole with a radius which is less than that of the corresponding strong magnetic beads, the strong magnetic beads projecting from an upper cover surface of the shell through the spherical through hole, each strong magnetic bead having elastic supporting equipment which comprises magnetic beads salver, a spring and a cavity for orientating the spring, the spring orientation cavity being fixed on an under cover of the shell, the spring is installed in the cavity and its upper end is held under the magnetic beads salver, the electromagnetic screw including an upper cover, rotating iron core, rotating iron core restoring spring, amortizing rubber mat, loop and loop spool, two helical grooves being provided on the external surface of the rotating iron core, each groove separately starting from two ends of the diameter of iron core upper surface and extending to the lower end in parallel, an interior of the upper cover having two salient assorted with the helical grooves, and the rubber mat being provided at the bottom of loop spool on the midplane.

10. A human massager, as claimed in claim 7 wherein the eletromagnetic screw being equipped with a rotating axial driving part and a fixing part, the strong electromagnetic rotating head being fixed together with the electromagnetic screw rotating driving part and driven by the electromagnetic screw rotating in an axial direction wherein there are two helical grooves for the external surface of the rotating iron core, each helical groove being starting separately from the two ends of the diameter of an iron core upper surface and spreading to the lower end with a rotation of at least 180 degrees, an interior of the upper cover having two salient assorted with the helical groove.

* * * * *